United States Patent
Heinz

(10) Patent No.: US 7,850,736 B2
(45) Date of Patent: Dec. 14, 2010

(54) VERTEBRAL FUSION IMPLANTS AND METHODS OF USE

(75) Inventor: Eric S. Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 596 days.

(21) Appl. No.: 11/403,348

(22) Filed: Apr. 13, 2006

(65) Prior Publication Data

US 2007/0270956 A1   Nov. 22, 2007

(51) Int. Cl.
*A61F 2/44* (2006.01)
(52) U.S. Cl. .................. 623/17.16; 623/17.11
(58) Field of Classification Search ... 623/17.11–17.16; D7/678
See application file for complete search history.

(56) References Cited

U.S. PATENT DOCUMENTS

| | | | | |
|---|---|---|---|---|
| D246,084 S | * | 10/1977 | Graves | ............ D7/678 |
| 5,522,899 A | | 6/1996 | Michelson | |
| 5,888,223 A | * | 3/1999 | Bray, Jr. | ............ 623/17.16 |
| 6,066,175 A | | 5/2000 | Henderson et al. | |
| 6,096,080 A | * | 8/2000 | Nicholson et al. | ........ 623/17.16 |
| 6,224,631 B1 | | 5/2001 | Kohrs | |
| 6,235,059 B1 | | 5/2001 | Benezech et al. | |
| 6,432,106 B1 | | 8/2002 | Fraser | |
| 6,436,141 B2 | | 8/2002 | Castro et al. | |
| 6,537,320 B1 | | 3/2003 | Michelson | |
| 6,607,530 B1 | | 8/2003 | Carl et al. | |
| D491,774 S | * | 6/2004 | Brousseau et al. | ........... D7/678 |
| D494,026 S | * | 8/2004 | Brousseau et al. | ........... D7/678 |
| 6,837,905 B1 | | 1/2005 | Lieberman | |
| 2003/0023306 A1 | | 1/2003 | Liu et al. | |
| 2003/0078587 A1 | * | 4/2003 | Lechot et al. | ................ 606/81 |
| 2003/0181981 A1 | | 9/2003 | Lemaire | |
| 2004/0092929 A1 | | 5/2004 | Zindrick | |
| 2004/0230305 A1 | | 11/2004 | Gorensek et al. | |
| 2005/0010234 A1 | | 1/2005 | Ralph et al. | |
| 2005/0131416 A1 | * | 6/2005 | Jansen et al. | ................ 606/86 |
| 2005/0283239 A1 | | 12/2005 | Crozet | |
| 2006/0058876 A1 | | 3/2006 | McKinley | |

OTHER PUBLICATIONS

SSR Surgical catalog, Joseph Rasp, p. 318, available Sep. 29, 2004, accessed May 7, 2009.*
Synthes, "Solution auto-stable pour les fusions intersomatiques par voie antérieure." SynFix-LR. 1 page.
Drawing. "SynFix as Standalone ALIF." Spine. Dec. 1, 2005. 1 page. vol. 30. No. 23.

* cited by examiner

*Primary Examiner*—Todd E Manahan
*Assistant Examiner*—Julianna N Harvey

(57) ABSTRACT

A vertebral implant for use in vertebral fusion surgeries includes a body with an exterior surface and an interior surface. The interior surface defines an interior cavity into which bone growth promoting materials such as bone graft are insertable. The body also includes a plurality of apertures that extend from the exterior surface to the interior surface. Further, the vertebral implant includes a cutting feature to decorticate bone that protrudes outward from the exterior surface at each aperture. The cutting feature is shaped so that as a cutting force is applied to move the implant in a cutting direction, the removed bone matter is directed through the apertures and into the interior cavity.

16 Claims, 10 Drawing Sheets

VERTEBRAL FUSION IMPLANTS AND METHODS OF USE

BACKGROUND

Vertebral implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. Motion between vertebral bodies is naturally provided in part by the flexible disc material that resides between adjacent vertebral bodies. Spinal fusion often involves the removal of the vertebral disc and insertion of an interbody implant to create a fused junction between a pair of vertebral bodies. Fusion may also occur at multiple vertebral levels or between vertebral bodies that are several levels apart. Interbody implants may be coated, filled, or surrounded by growth promoting materials such as BMP, DBM, allograft, autograft or other osteoinductive growth factors to facilitate fusion between the vertebral bodies and the implant.

Conventionally, interbody implants are inserted into the space between vertebral bodies after the disc material has been removed and after the vertebral end plates are prepared. This end plate preparation may include shaping, planing, scraping, or other decorticating processes in which bone matter is removed and blood flow is initiated to enhance bone growth into the interbody implant. Ideally, new bone matter forms and bridges the gap between the vertebral bodies and the growth promoting material. In certain instances, particularly where the growth promoting material is contained within the interbody implant, new bone matter does not sufficiently span the gap between the vertebral endplate and the growth promoting material. Consequently, the fusion site may be compromised.

SUMMARY

Illustrative embodiments disclosed herein are directed to a vertebral implant for use in vertebral fusion surgeries. The vertebral implant includes a body with an exterior surface and an interior surface. The body may be shaped for use in ALIF, PLIF, and TLIF surgeries. The interior surface defines an interior cavity into which bone growth promoting materials such as bone graft are insertable. The body also includes a plurality of apertures that extend from the exterior surface to the interior surface. Further, the vertebral implant includes a cutting feature to decorticate bone that protrudes outward from the exterior surface at each aperture.

The cutting features may be oriented to cut in one direction or a plurality of directions. The cutting features may be oriented to cut bone material upon the application of a rotation force to the vertebral implant. The cutting features may be oriented to cut bone material upon the application of a non-rotating pushing or pulling force to the vertebral implant. The cutting features may vary in height such that moving the vertebral implant in a cutting direction causes more bone material to be removed by cutting features disposed towards a trailing end of the implant. Further, cutting features may be oriented to cut bone material upon the application of a reciprocating force to the vertebral implant. The cutting features may be shaped so that as a cutting force is applied to move the implant in a cutting direction, the removed bone matter is directed through the apertures and into the interior cavity.

DETAILED DESCRIPTION

Figure 1:
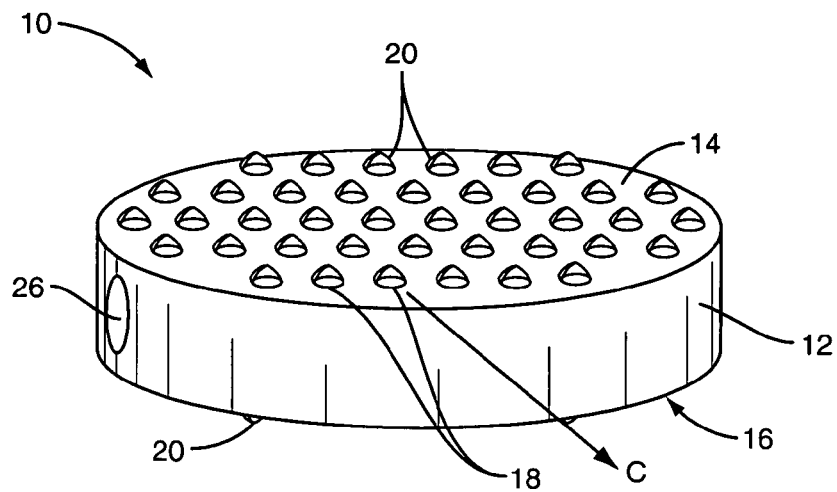
FIG. 1 is a perspective view of a vertebral implant according to one embodiment.

The various embodiments disclosed herein relate to a vertebral implant in which bone-contact surfaces are constructed with cutting features that remove bone matter from vertebral bodies in the human spine. Further, the cutting features are configured to guide the removed bone matter through apertures in the vertebral implant and into contact with bone-growth-promoting material contained therein. Reference number 10 in FIG. 1 generally identifies one example of an implant with cutting features on the bone-contact surfaces. The representative vertebral implant 10 is illustrated as a disc replacement implant that is inserted between vertebral bodies of a patient as part of a disc replacement surgery. The exemplary vertebral implant 10 includes a perimeter wall 12 that extends between a superior surface 14 and an inferior surface 16. The superior surface 14 and inferior surface 16 are bone-contact surfaces in that they are positioned adjacent to and face a vertebral endplate once the vertebral implant 10 is inserted into a patient.

The vertebral implant 10 shown in FIG. 1 includes a simple disc shape, though other shapes and contours may be used. In further embodiments, the vertebral implant 10 may take on other types of configurations, such as, for example, a circular shape, kidney shape, semi-oval shape, bean-shape, D-shape, elliptical-shape, egg-shape, or any other shape that would occur to one of skill in the art. The vertebral implant 10 may take on substantially solid configurations, such as, for example, block-like or plate-like configurations that do not define an open inner region. In other embodiments, the vertebral implant 10 could also be described as being annular, U-shaped, C-shaped, V-shaped, horseshoe-shaped, semi-circular shaped, semi-oval shaped, or other similar terms defining an implant including at least a partially open or hollow construction.

The vertebral implant 10 may be constructed from biocompatible metal alloys such as titanium, cobalt-chrome, and stainless steel. The vertebral implant 10 may be constructed from non-metallic materials, including for example, ceramics, resins, or polymers, such as UHMWPE and implantable grade polyetheretherketone (PEEK) or other similar materials (e.g., PAEK, PEKK, and PEK). The vertebral implant 10 may be constructed of synthetic or natural bone or bone composites. Those skilled in the art will comprehend a variety of other material choices that are suitable for the illustrated vertebral implant 10.

The exemplary vertebral implant 10 includes a plurality of apertures 18 disposed about the superior surface 14. The apertures 18 are shown as substantially cylindrical, though it should be understood that other shapes, including for example, square, hex, triangular, diamond, crescent, elliptical apertures may be used. Additional apertures 18 are also disposed about the inferior surface 16, though their existence is not immediately apparent from FIG. 1. In an alternative embodiment, the apertures 18 are disposed about one of the superior 14 and inferior 16 surfaces but not the other. The vertebral implant 10 also includes one or more side apertures 26 disposed about the perimeter wall 12. The side apertures 26 provide a passage from the exterior of the vertebral implant into an interior cavity 30 that is more clearly visible in FIG. 2 and discussed in greater detail below. The side apertures 26 may also provide a location at which to grasp the vertebral implant 10 during surgical installation.

In the illustrated embodiment, a cutting feature 20 is associated with each aperture 18. In other embodiments, the vertebral implant 10 may have apertures without associated cutting features 20 or cutting features 20 without associated apertures 18. The cutting features 20 may be implemented as teeth, hooks, serrations, blades, or other features adapted to remove cortical bone from a vertebral body as the vertebral implant 10 is inserted. The cutting features 20 may be constructed of the same material as the remainder of the vertebral implant 10 as described above. In one embodiment, the cutting features 20 are constructed of rigid, hardened materials such as titanium, ceramic, or polymers impregnated with carbon fibers. In the embodiment illustrated in FIG. 1, the cutting features 20 are oriented in a common direction so as to define a cutting direction C. As described below, this cutting direction C may coincide with the insertion direction. Accordingly, the vertebral implant 10 may include an insertion feature 36 to which an insertion tool (see FIG. 4) may be attached. The insertion feature 36 may be an aperture, such as a threaded hole or a slot that is engageable by a male insertion tool. Alternatively, the insertion features 36 may be a protruding feature that is engageable by a female insertion tool.

Figure 2:
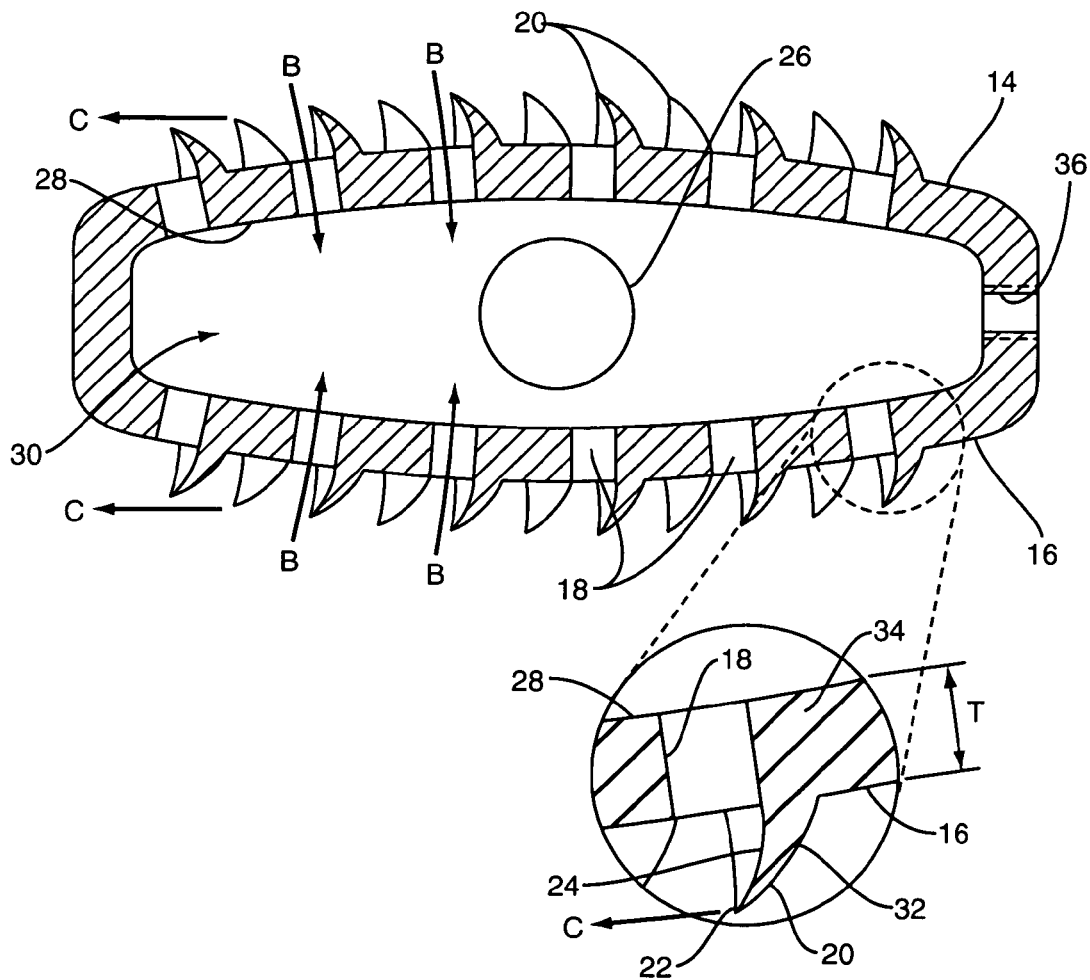
FIG. 2 is a side section view, including a partial detail, of a vertebral implant according to one embodiment.

The lateral cross section view of the vertebral implant 10 provided in FIG. 2 shows the aforementioned interior cavity 30. This cavity 30 is defined in part by an interior surface 28. In the embodiment shown, the interior surface 28 follows a contour similar to the outer surfaces 12, 14, 16 of the vertebral implant such that the thickness T of wall 34 is approximately the same throughout. In other embodiments, the interior cavity 30 may include a different shape than the outer geometry of the vertebral implant 10. In either case, the interior cavity 30 is configured to receive bone growth promoting material such as BMP, DBM, allograft, autograft or other osteoinductive growth factors to facilitate fusion between vertebral bodies and the implant 10. The apertures 18 disposed about the superior surface 14 and inferior surface 16 provide a passage through which blood and removed bone material may pass from outside the vertebral implant 10 to the interior cavity 30 where the bone growth promoting material is placed. This removed bone material may be scoured by the cutting features 20 and diverted through the apertures 18 into the interior cavity 30 as denoted by the arrows labeled B.

The right side of FIG. 2 also depicts a detail view of the exemplary cutting features 20. The cutting features 20 extend generally outward from the superior surface 14 and inferior surface 16. Relative to the cutting direction C, the cutting features 20 include a leading surface 24 and a trailing surface 32. The leading surface 24 and trailing surface 32 curve generally towards the cutting direction C. This curvature improves the overall strength and cutting ability of the cutting features 20. Further, the leading surface 24 and the trailing surface converge at a cutting edge 22 that is advantageously sharpened to allow the cutting feature 20 to remove bone material from vertebral bodies during implant 10 insertion. Notably, the cutting feature 20 is raked in the cutting direction such that the cutting edge 22 is disposed at least partly above the aperture 18 with which the cutting feature 20 is associated.

Figure 3:
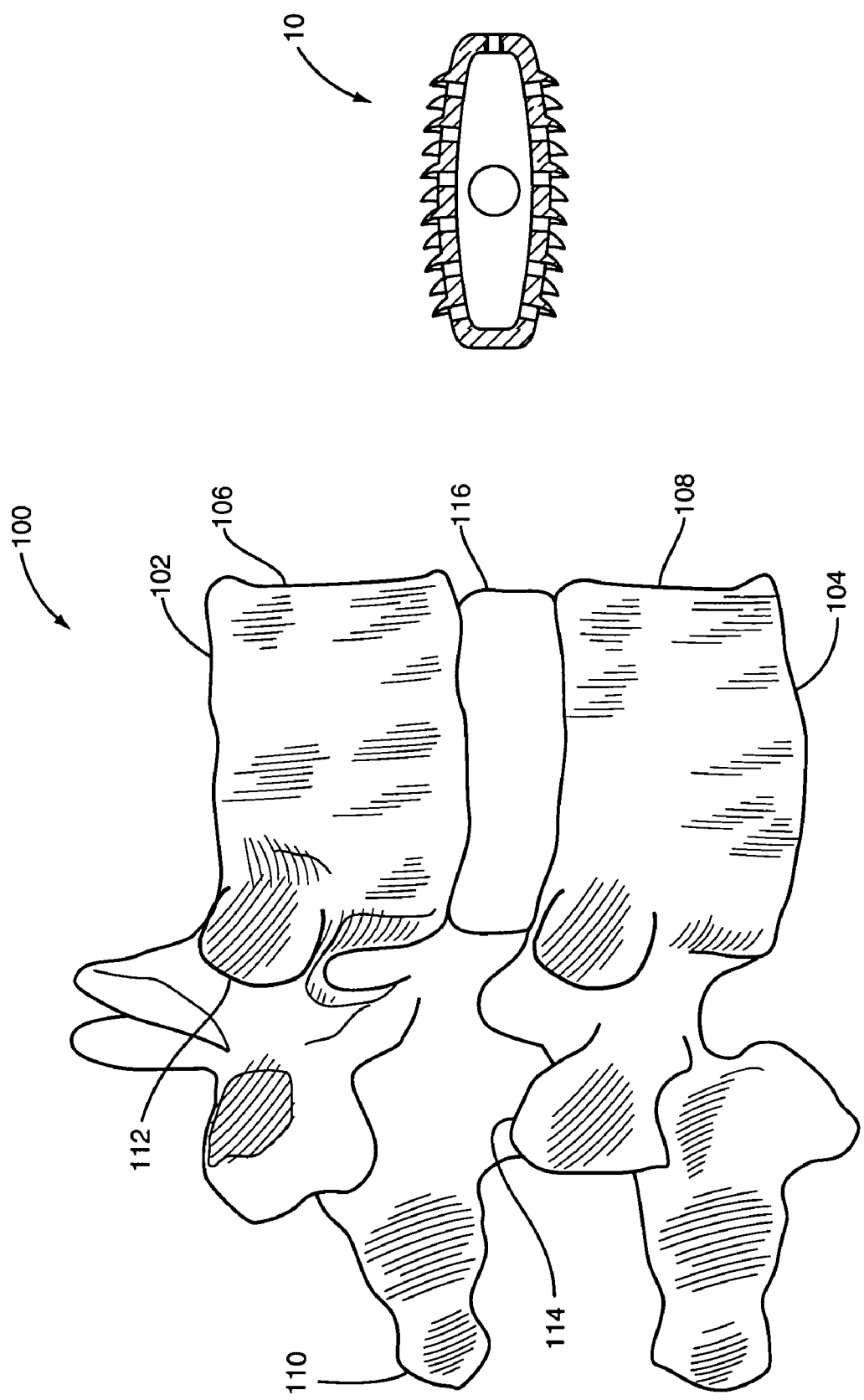
FIG. 3 is a side section view of a vertebral implant according to one embodiment shown relative to vertebral bodies.
Figure 4:
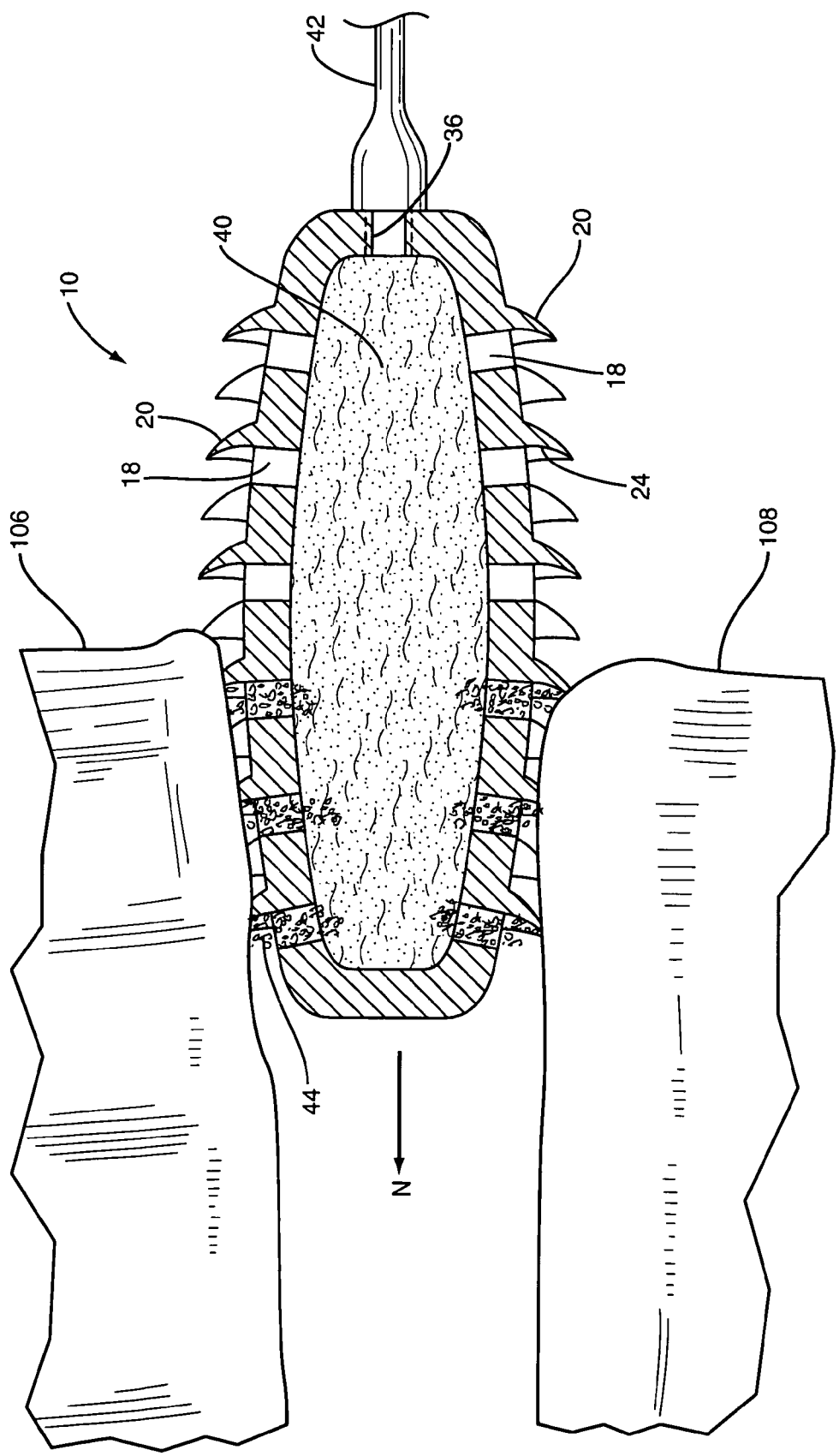
FIG. 4 is a side section view of a vertebral implant according to one embodiment shown relative to vertebral bodies.
Figure 5:
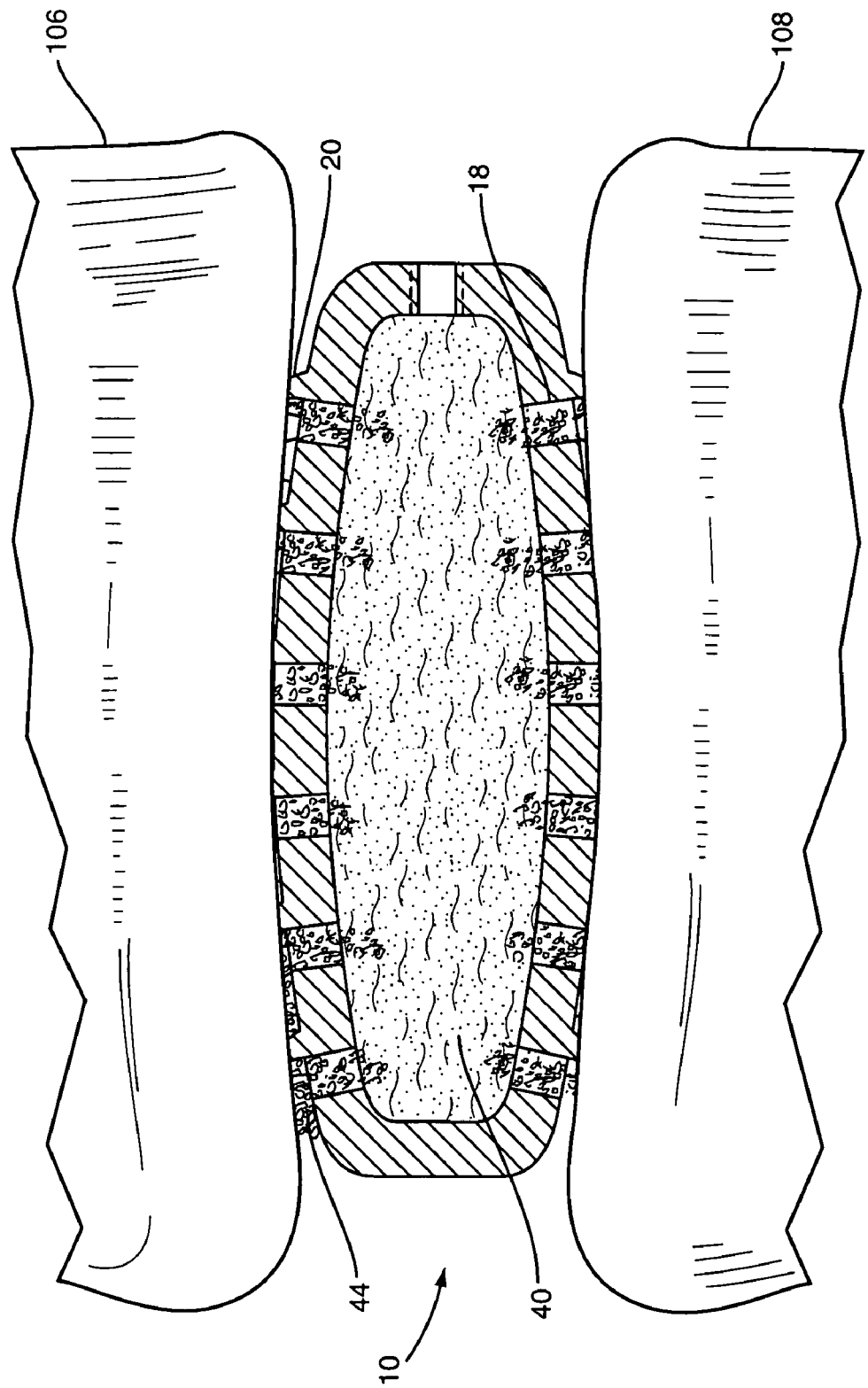
FIG. 5 is a side section view of a vertebral implant according to one embodiment shown relative to vertebral bodies.

In the depicted embodiment, the leading surface 24 of the cutting feature 20 extends generally upward from the aperture 18 in the walls 34 of the vertebral implant 10. In this configuration, the leading surface 24 and aperture 18 share a common wall. Thus, the cutting feature 20 curves at least partly around the aperture. In other embodiments, the aperture 18 may have straight sides and the leading surface 24 may share one or more sides of the aperture 18. Further, the leading surface 24 is generally concave, bent, or curved in the direction of the aperture 18. Consequently, through motion of the vertebral implant 10 in the cutting direction C, the leading surface 24 tends to divert removed bone matter through the aperture 18, past the interior surface 28 and into the interior cavity 30. FIGS. 3, 4, and 5 illustrate this sequence, which occurs as the vertebral implant 10 is inserted into a patient.

Specifically, FIG. 3 shows two vertebrae 102, 104 and a disc 116 therebetween. Each vertebra 102, 104 includes a generally cylindrical body 106, 108 that contributes to the primary weight-bearing portion of the spine 100. Further, each vertebra 102, 104 includes various bony processes 110, 112 extending posterior to the body 106, 108. Adjacent vertebrae 102, 104 may move relative to each other via facet joints 114 and due to the flexibility of the disc 116. For instances where the disc 116 is herniated or degenerative, the entire disc 116 may be replaced with the vertebral implant 10 using an anterior approach as shown.

Initially, the disc 116 is removed from the space between the vertebrae 102, 104. Also, the vertebral implant 10 is packed with a bone growth promoting material such as those described above. The bone growth promoting material is identified by numeral 40 in FIG. 4. FIG. 4 also shows an insertion tool 42 attached to the vertebral implant 10. Using the insertion tool 42, the vertebral implant 10 is guided towards and between the vertebral bodies 106, 108. An insertion force is applied in the direction of the arrow labeled N. This insertion force causes the cutting features 20 to engage and remove bone matter from the vertebral bodies 106, 108. This bone matter is identified by number 44 in FIG. 4. The shape and configuration of the cutting feature 20, and specifically leading surface 24, tend to guide the removed bone matter 44 from the exterior of the vertebral implant 10, through the apertures 18, into the interior cavity 30, and into contact with the bone growth promoting material 40.

Ultimately, once the vertebral implant 10 is inserted completely between the vertebral bodies 106, 108 as shown in FIG. 5, the insertion tool 42 may be removed. At this juncture, bone matter 44 has been removed by the cutting features 20 and packed through the apertures 18. Some of the removed bone matter 44 travels through the apertures 18 and into contact with the bone growth promoting materials 40. Some of the removed bone matter 44 remains in the apertures 18. Further, some of the removed bone matter 44 remains near the cutting features 20 and adjacent to the vertebral bodies 106, 108. Accordingly, a bridge comprising bone matter 44 is formed between the vertebral bodies 106, 108 and the bone growth promoting material 40.

Figure 6:
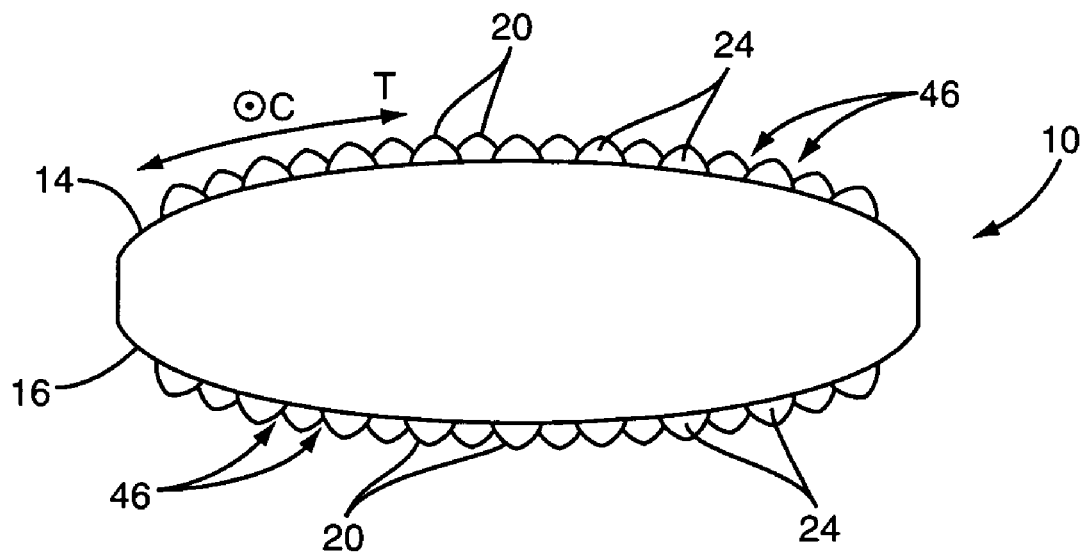
FIG. 6 is a front view of a vertebral implant according to one embodiment.

FIG. 6 shows a frontal view of the exemplary vertebral implant 10. In this orientation, the cutting direction C described above is directed out of the page. FIG. 6 specifically illustrates an overlapping configuration for the plurality of cutting features 20 and leading surfaces 24 on both the superior surface 14 and inferior surface 16. The overlap is in a direction T that is substantially parallel to the superior surface 14 (and inferior surface 16), but transverse to the cutting direction C. The cutting features 20 may be disposed in a staggered configuration such that they overlap across multiple rows oriented in the transverse direction T. In other words, the cutting features 20 shown in FIG. 6 may be arranged in a single row in the transverse direction T or at different depths into or out of the page to achieve the overlapping configuration. As a result, the cutting features 20 are able to remove significant amounts of bone matter from the vertebral bodies 106, 108 as the vertebral implant 10 is inserted in the cutting direction C.

In one embodiment, the cutting features 20 overlap one another in the transverse direction T by an amount that leaves a nominal space 46 between the cutting features 20. This space 46 may permit the removed bone matter 44 to fill gaps between the vertebral implant 10 and the vertebral bodies 106, 108. That is, the space 46 strikes a balance between directing all removed bone matter 44 into the interior cavity 30 of the vertebral implant 10 and allowing the removed bone matter 44 to fill gaps between the vertebral implant 10 and the vertebral bodies 106, 108.

Figure 7:
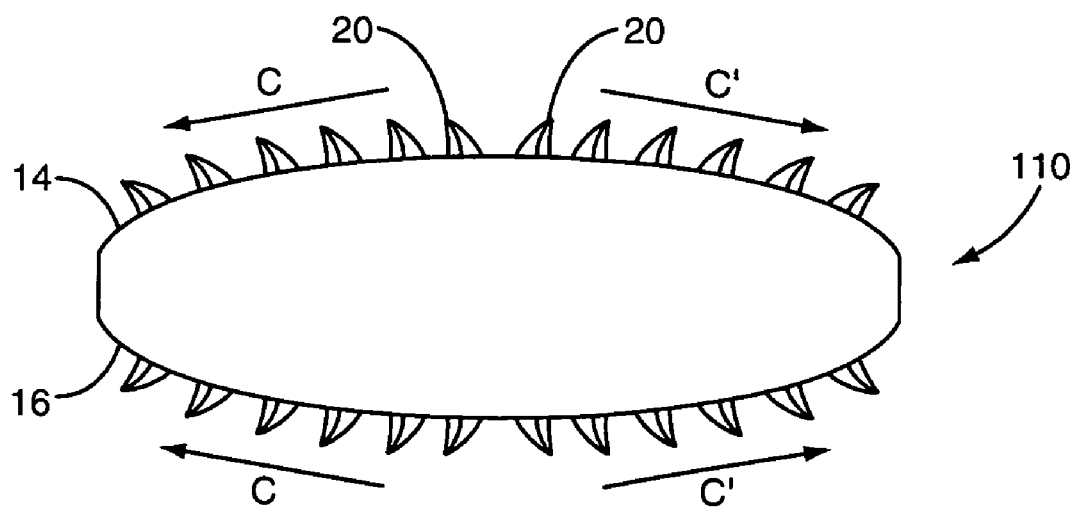
FIG. 7 is a side view of a vertebral implant according to one embodiment.
Figure 8:
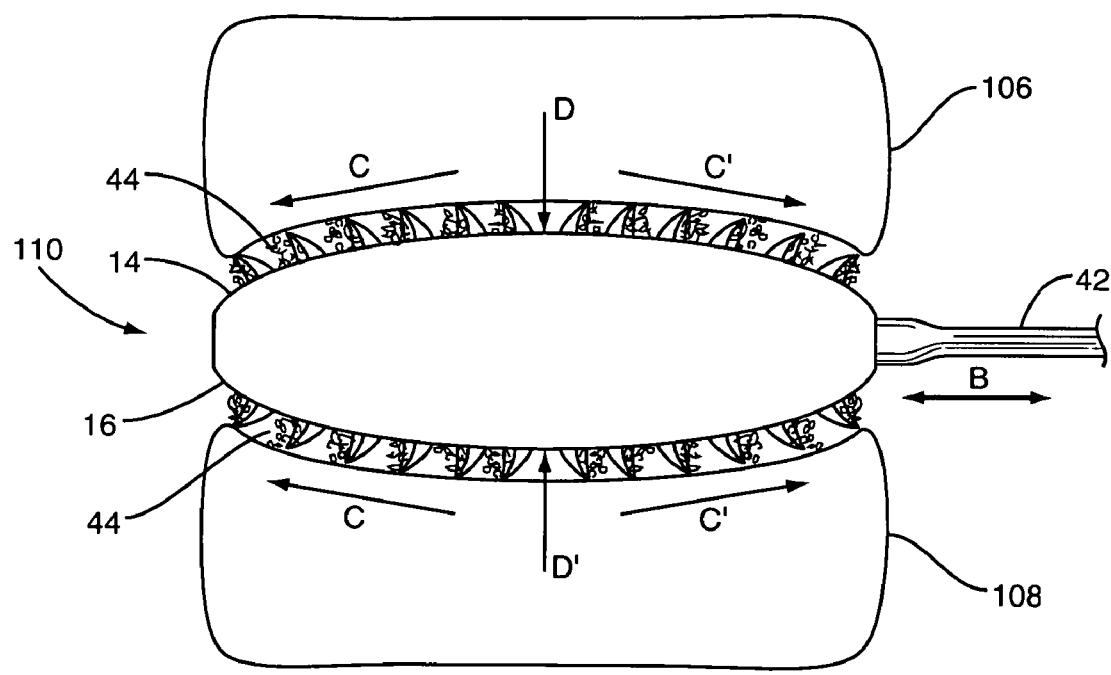
FIG. 8 is a side view of a vertebral implant according to one embodiment shown relative to vertebral bodies.
Figure 9:
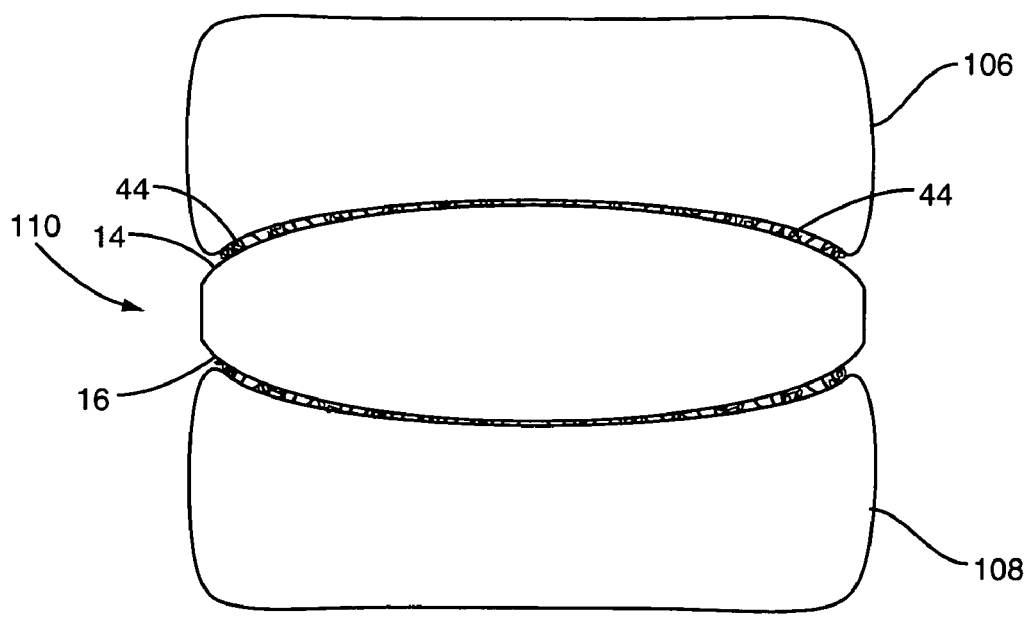
FIG. 9 is a side view of a vertebral implant according to one embodiment shown relative to vertebral bodies.

Embodiments described above included a plurality of cutting features 20 arranged along a common cutting direction C. In the embodiment of the vertebral implant 110 shown in FIG. 7, some of the cutting features 20 are arranged in a first cutting direction C while other cutting features 20 are arranged in a second, different cutting direction C'. With the cutting features 20 configured in this manner, a surgeon may be able to remove additional bone matter 44 by imparting a reciprocating motion as indicated by the arrows labeled B in FIG. 8. The reciprocating motion B may be imparted through an insertion tool 42. With each pass in the forward and backward direction, the cutting features 20 are able to remove more bone matter 44. Ultimately, as FIG. 9 shows, if enough bone matter 44 is removed, the cutting features 20 dig into the cortical bone of the vertebral bodies 106, 108 by an amount sufficient to bring the vertebral bodies (in the directions D, D') into close proximity with the superior surface 14 and the inferior surface 16 of the vertebral implant 110.

Figure 10:
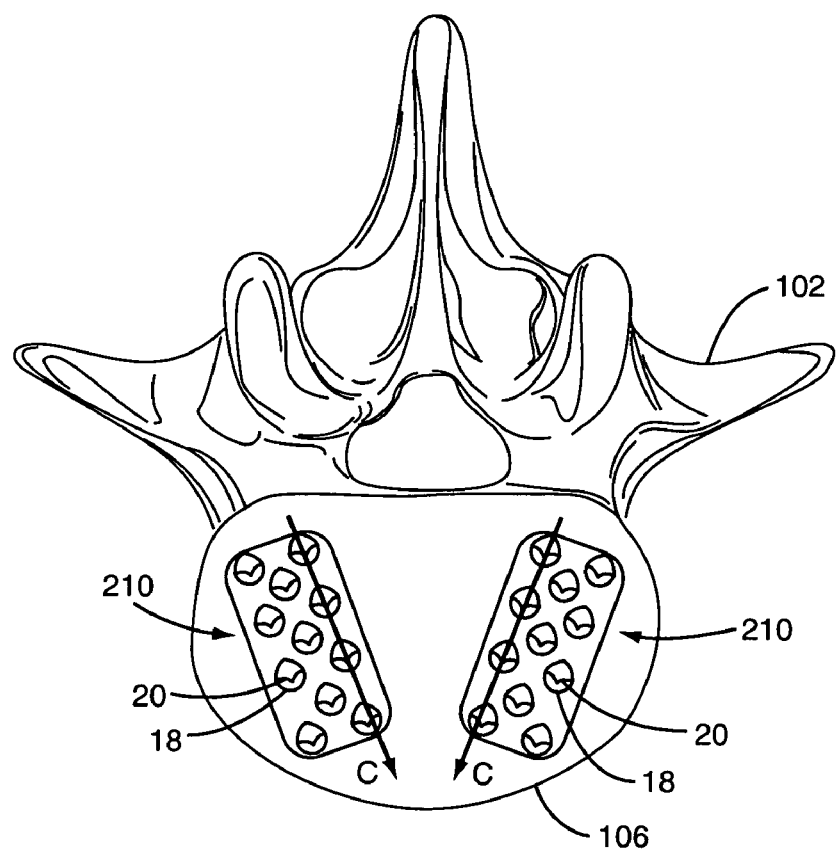
FIG. 10 is a top view of a vertebral implant according to one embodiment shown relative to a vertebral body.

The cutting features 20 may be incorporated on different types of fusion implants, including ALIF cages similar in structure to the above-described embodiments. The cutting features 20 may be incorporated in PLIF or TLIF cages as well. FIGS. 10, 11, 12, and 13 illustrate embodiments of this type that may be inserted from a posterior, transforaminal, or lateral direction. FIG. 10 shows one implementation where vertebral implants 210 are inserted using a posterior approach. Accordingly, the vertebral implants 210 include a plurality of cutting features 20 adapted as described above to remove bone matter from vertebral body 106 as the vertebral implants 210 are inserted in the cutting direction C. Concurrent with the action of cutting bone matter from the vertebral body 106, the cutting features 20 direct at least some of the bone matter through the apertures 18 into an interior cavity (not shown) in the vertebral implant 210.

Figure 11:
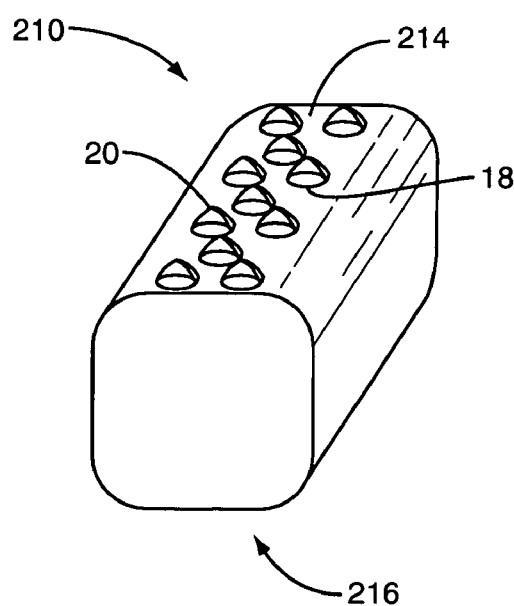
FIG. 11 is a perspective view of a vertebral implant according to one embodiment.

The vertebral implants 210 may include a generally rectangular shape as depicted in the perspective view in FIG. 11. In this embodiment, the cutting features 20 are included in one or both of the superior surface 214 and inferior surface 216. The lateral surfaces 212 may include apertures 18 and/or cutting features 20, though neither is shown in FIG. 11.

Figure 12:
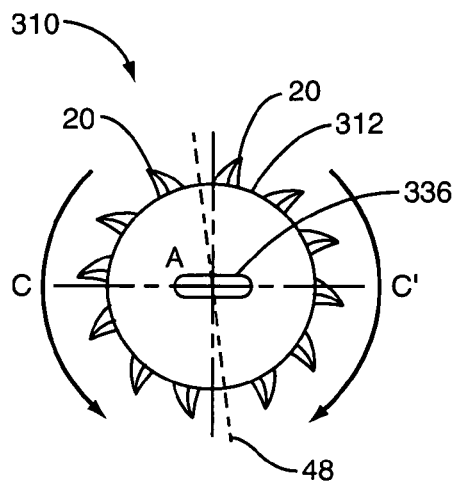
FIG. 12 is a front view of a vertebral implant according to one embodiment.
Figure 13:
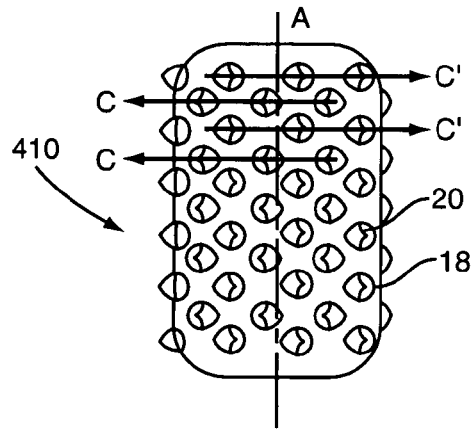
FIG. 13 is a top view of a vertebral implant according to one embodiment.

In one embodiment shown in FIGS. 12 and 13, the vertebral implants 310, 410 include a generally cylindrical shape. In each embodiment, the cylindrically shaped implant 310, 410 extends along a longitudinal axis A. Each vertebral implant 310, 410 may be inserted along this longitudinal axis A. FIG. 12 shows an end view of a vertebral implant 310 where cutting features 20 are disposed about the cylindrical outer wall 312. Furthermore, the cutting features 20 are arranged to create two different cutting directions C and C' that traverse a substantially arcuate path. Specifically, the cutting features on the left side of the dashed line 48 in FIG. 12 are oriented in a first direction associated with cutting direction C. The cutting features on the right side of the dashed line in FIG. 12 are oriented in a second direction associated with cutting direction C'. Notably, the cutting directions C, C' do not necessarily coincide with the direction of insertion, which may be along the longitudinal axis A.

The vertebral implant 310 may include an insertion feature 336 to which an insertion tool (not shown) may be attached. The insertion feature 336 may be elongated or may comprise multiple features disposed on opposite sides of the longitudinal axis A. This type of insertion feature may allow a surgeon to impart a rotating, reciprocating motion about axis A, in the two different cutting directions C and C' to remove bone matter along a generally cylindrical pattern. This rotating motion is in contrast with the non-rotating motion imparted on previously described embodiments to remove the bone matter.

FIG. 13 shows another embodiment of a cylindrically-shaped vertebral implant 410. In embodiments disclosed above, cutting features 20 that are facing different cutting directions were generally grouped in different portions of the implant (see e.g., FIG. 7 or FIG. 12). However, as FIG. 13 shows, the cutting features 20 may be oriented so that different cutting directions C, C' are interspersed about the vertebral implant 410. This configuration may be implemented in the different types of vertebral implants, including the PLIF, TLIF, and ALIF implants.

Figure 14:
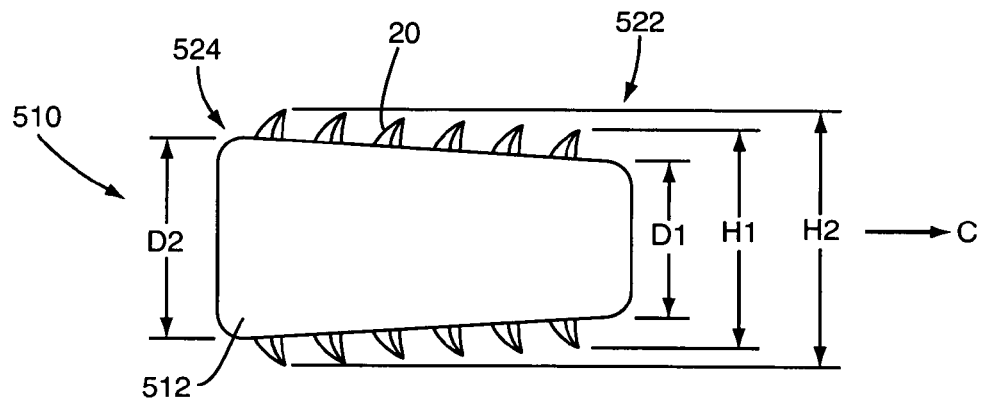
FIG. 14 is a side view of a vertebral implant according to one embodiment.
Figure 15:
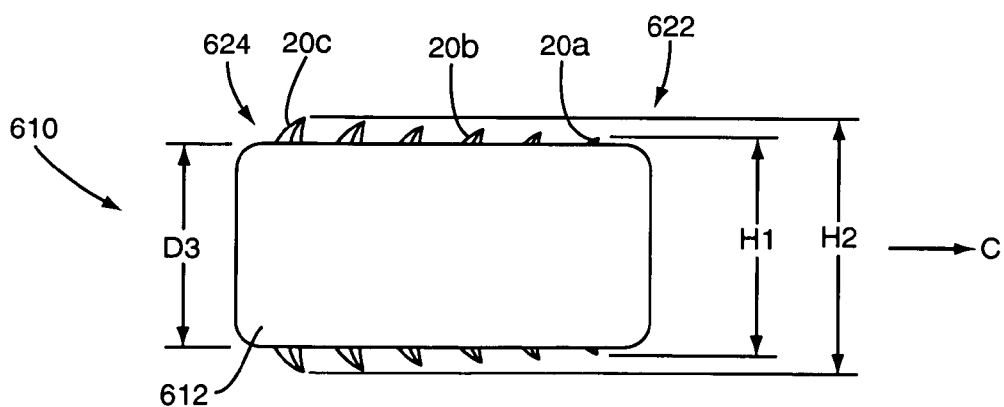
FIG. 15 is a side view of a vertebral implant according to one embodiment.

The cutting features 20 may be arranged at gradually increasing heights in a manner similar to a broach. FIGS. 14 and 15 illustrate examples of vertebral implants 510, 610 where the cutting features 20 are arranged at progressively taller heights. In both embodiments of the vertebral implant 510, 610, the cutting height increases from a leading end 522, 622 (relative to the cutting direction C) to a trailing end 524, 624 of the implant 510, 610. That is, the cutting features 20 disposed towards the leading end 522, 622 include a first associated height H1. However, the cutting features 20 disposed towards the trailing end 524, 624 include a larger, second associated height H2.

In the first exemplary embodiment, the cutting features 20 are substantially the same size. Therefore, the increase in height of the cutting features 20 primarily derives from an increase in the height of the implant body 512 from a first height D1 at the leading end 522 to a larger second height D2 at the trailing end 524. Alternatively, the increase in height may be obtained through different size cutting features 20a, 20b, 20c as shown in FIG. 15. In this embodiment, the height D3 of the implant body 612 remains substantially the same. However the cutting features 20a disposed near the leading end 622 of the vertebral implant 610 are smaller than cutting features 20b, 20c disposed towards the trailing end 624 of the vertebral implant 610. In one embodiment, the increase in height of the cutting features 20 may be obtained through a combination of a change in contour of the implant body 610 and a change in size of the cutting features 20.

Figure 16:
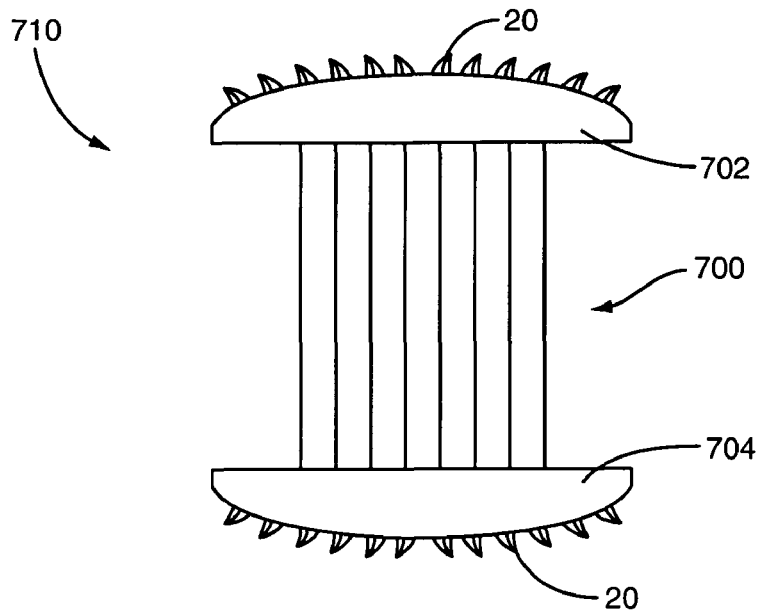
FIG. 16 is a side view of a vertebral implant according to one embodiment.

Embodiments described above related to vertebral implants that are implanted into the space normally occupied by a vertebral disc. In other procedures, such as vertebrectomies or corpectomies, one or more vertebral bodies are removed and an implant is inserted in the space left by the removed vertebrae. These types of devices, such as the vertebral implant 710 shown in FIG. 16, include multiple components, including spacers, a cage, rods, or other fixed or expandable members 700 spanning a distance between first and second end plates 702, 704. The various types and arrangements for the cutting features 20 described above may be used with these types of devices as well as those disclosed above. That is, the cutting features 20 may be disposed on separate end plates 702, 704 and not on the same body as disclosed in other embodiments.

Figure 17:
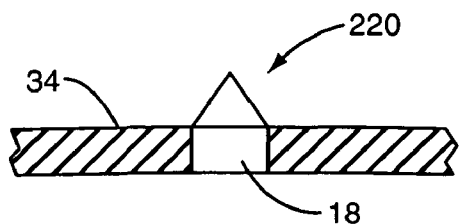
FIG. 17 is a partial section view of a vertebral implant illustrating a profile of a cutting feature according to one embodiment.
Figure 18:
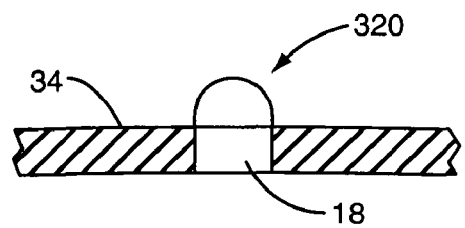
FIG. 18 is a partial section view of a vertebral implant illustrating a profile of a cutting feature according to one embodiment.
Figure 19:
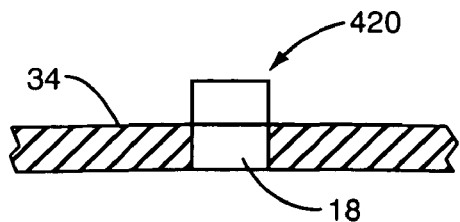
FIG. 19 is a partial section view of a vertebral implant illustrating a profile of a cutting feature according to one embodiment.
Figure 20:
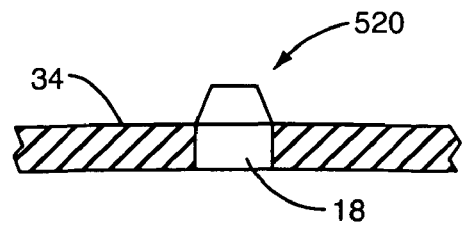
FIG. 20 is a partial section view of a vertebral implant illustrating a profile of a cutting feature according to one embodiment.

The cutting features 20 illustrated in FIGS. 1-16 include similar geometries. As described above, the leading surface 24 and trailing surface 32 of the cutting feature 20 intersect at a generally arcuate leading edge 22. In other embodiments, the cutting features may include different geometries that include straight, tapered, flared, or blunt geometries. FIGS. 17-20 illustrate some exemplary geometries that may be used for the cutting features. For instance, the cutting feature 220 may be triangular, pyramid-like, or diamond-like as shown in FIG. 17. In FIG. 18, the exemplary cutting feature 320 is generally dome or oval-shaped. FIG. 19 depicts an embodiment where the cutting feature 420 is squared while FIG. 20 depicts a generally trapezoidal cutting feature 520. Accordingly, the shape of the cutting features may be varied to achieve different cutting characteristics and/or to remove different amounts and different sizes of bone fragments. Each of these exemplary cutting features may be raked towards the cutting direction as in previously described embodiments. Further each of these exemplary cutting features may extend at least partially around the aperture with which the cutting feature is associated.

Figure 21:
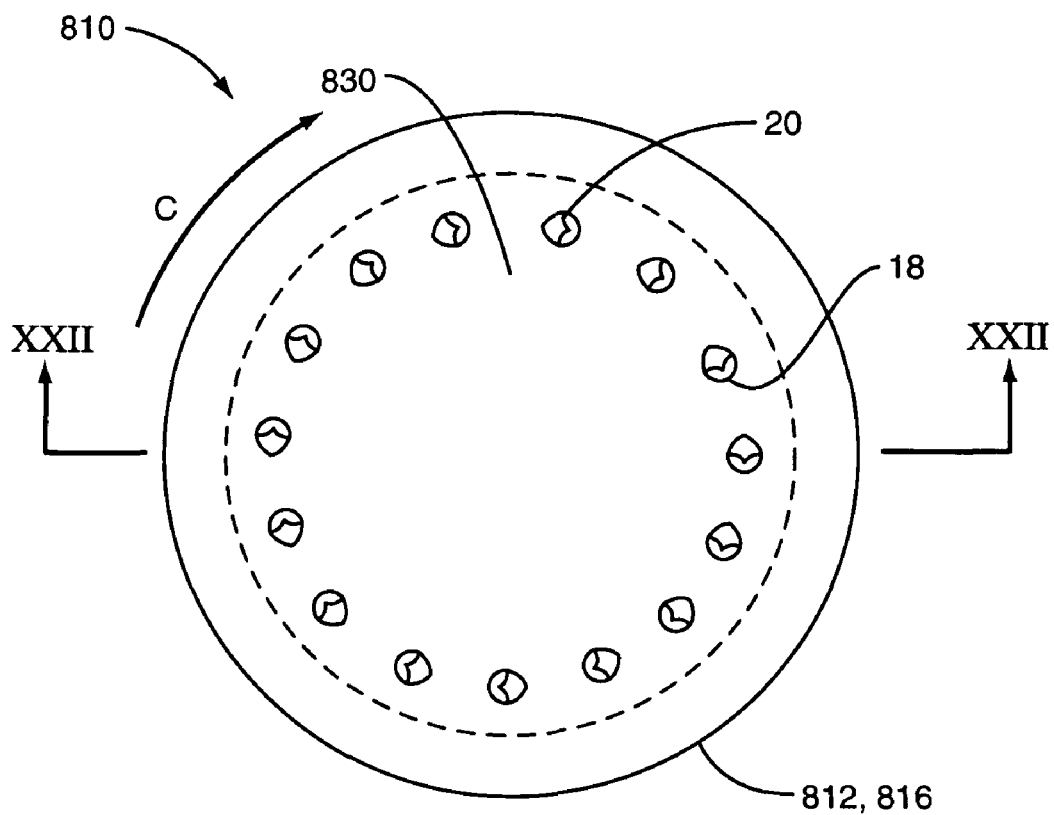
FIG. 21 is a top view of a vertebral implant according to one embodiment.
Figure 22:
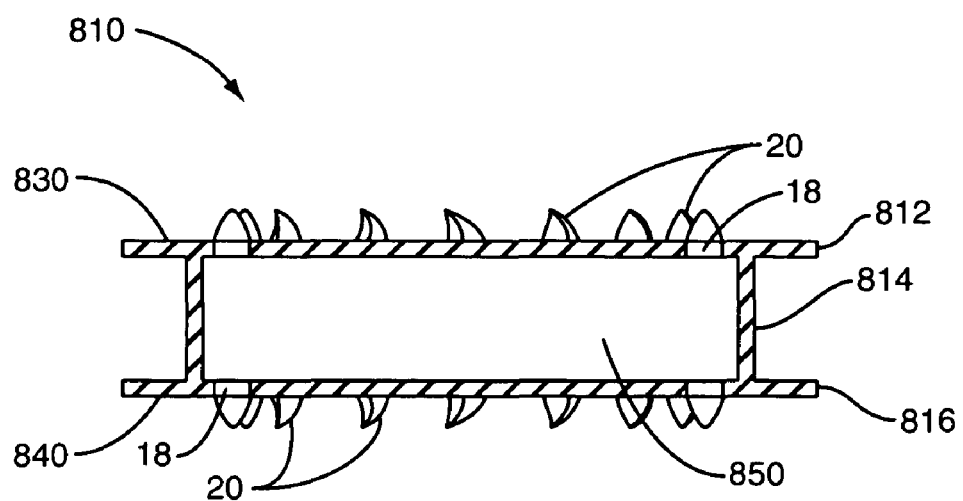
FIG. 22 is a side section view of a vertebral implant according to one embodiment.

In one embodiment shown in FIGS. 21 and 22, the vertebral implant 810 includes a generally cylindrical shape with a generally circular outer perimeter 812, 816. A cylindrical column 814 that includes a smaller diameter compared to the outer perimeter 812, 816 is disposed in a central portion of the vertebral implant 810, between end surfaces 830, 840. The vertebral implant 810 further includes an interior volume 850 that may be packed with a bone growth promoting material as previously described. The vertebral implant 810 includes superior 830 and inferior 840 surfaces that are positioned adjacent to vertebral endplates when the implant is inserted. As with previously described embodiments, the vertebral implant 810 includes cutting features 20 associated with apertures 18 that permit bone material to pass from the cutting features 20 and into an interior volume 850. The cutting features 20 may be disposed on both superior 830 and inferior 840 surfaces.

As FIG. 21 shows, the cutting features 20 are disposed in a radial manner so that the cutting direction follows an arcuate path defined by the orientation of the cutting features 20. The cutting features 20 may include substantially similar heights or may gradually increase or decrease in height around the perimeter 812, 816 of the implant 810 as described above. Though not illustrated, additional cutting features may be disposed interior to the depicted cutting features 20. Further the cutting features 20 may be oriented along the same cutting direction or different cutting directions than those illustrated in FIG. 21. The vertebral implant 810 may be inserted between vertebral bodies and rotated in the cutting direction by engaging the implant 810, for example at surface 814, with an unillustrated insertion tool. As described above, the cutting features 20 may be aligned along a common cutting direction or different cutting directions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, aside from the disclosed apertures 18 and cutting features 20, embodiments disclosed above have not included any particular surface geometry, coating, or porosity as are found in conventionally known vertebral implants. Surface features such as these are used to promote bone growth and adhesion at the interface between an implant and a vertebral body. Examples of features used for this purpose include, for example, teeth, scales, keels, knurls, and roughened surfaces. Some of these features may be applied through post-processing techniques such as blasting, chemical etching, and coating, such as with hydroxyapatite. The superior and inferior bone interface surfaces of the vertebral implant may also include growth-promoting additives such as bone morphogenetic proteins. Alternatively, pores, cavities, or other recesses into which bone may grow may be incorporated via a molding process. Other types of coatings or surface preparation may be used to improve bone growth into or through the bone-contact surfaces. The present embodiments are, therefore, to be considered in all respects as illustrative and not restrictive, and all changes coming within the meaning and equivalency range of the appended claims are intended to be embraced therein.

What is claimed is:

1. An implant for insertion into a patient between first and second vertebral members, the implant comprising:
   a body including first and second exterior walls and sidewalls that extend between the first and second exterior walls that form an enclosed interior cavity into which bone growth promoting materials are insertable, the body sized and configured to fit within an intervertebral space with the first wall facing towards the first vertebral member and the second wall facing towards the second vertebral member when the implant is inserted into the patient;
   a plurality of apertures extending through each of the first and second walls and into the interior cavity;
   the plurality of apertures being spaced apart along a length and a width of each of the first and second walls; and
   a plurality of cutting features to decorticate the vertebral members with one of the plurality of cutting features protruding outward from the body at each aperture, each of the plurality of cutting features including a leading surface and a trailing surface, the leading surface and the trailing surface intersecting at a cutting edge that is at least partly disposed over the aperture;
   wherein a first cutting feature includes a first leading surface facing a first cutting direction and a second cutting feature includes a second leading surface facing a different second cutting direction.

2. The implant of claim 1 wherein the exterior surface of the body is substantially cylindrical.

3. The implant of claim 1 wherein the plurality of apertures are spaced away from the sidewalls.

4. The implant of claim 1 further comprising a second plurality of apertures positioned along the first and second walls, the second plurality of apertures being spaced away from the cutting features.

5. The implant of claim 1 wherein each of the cutting features includes a leading surface that is curved in a cutting direction to be partially disposed over the corresponding aperture.

6. An implant for insertion into a patient between first and second vertebral members, the implant comprising:
   a hollow body with first and second walls that form an enclosed interior cavity into which bone growth promoting materials are insertable, the first wall contacting against the first vertebral member and the second wall contacting against the second vertebral member after the implant has been inserted into the patient;
   a plurality of apertures extending through each of the first and second walls and being spaced apart along a length and a width of each of the first and second walls;
   a cutting feature disposed protruding outward from the body at each aperture, the cutting feature including a leading surface relative to a cutting direction, the leading surface extending at least partly around the aperture, and the leading surface being concave relative to the aperture; and
   a plurality of second cutting features that extend outward from the first and second walls, the plurality of second cutting features being spaced away from each of the apertures;
   the enclosed interior cavity configured to capture and maintain portions of the first and second vertebral members that are cut by the cutting features and enter the enclosed interior cavity through the plurality of apertures.

7. The implant of claim 6 wherein the exterior surface of the body is substantially cylindrical.

8. The implant of claim 6 wherein a first cutting feature includes a first leading surface facing a first cutting direction and a second cutting feature includes a second leading surface facing a different second cutting direction.

9. The implant of claim 6 wherein the cutting features at least partially overlap in a direction substantially parallel to an exterior surface and transverse to the cutting direction.

10. The implant of claim 6 wherein the body includes sidewalls that extend between the first and second walls with the plurality of apertures being spaced away from the sidewalls.

11. The implant of claim 6 further comprising a plurality of second apertures that extend through each of the first and second walls and are spaced away from each of the cutting features.

12. The implant of claim 6 wherein the cutting feature extends over only a portion of the aperture.

13. An implant for insertion into a patient between first and second vertebral members, the implant comprising:
   a hollow body with an enclosed interior space, the enclosed interior space formed at least partially by a first exterior wall that faces towards the first vertebral member and a second exterior wall that faces towards the second vertebral member when the implant is inserted into the patient;
   a plurality of features positioned about a length and a width of the first exterior wall, each of the plurality of features includes an aperture that extends through the first exterior wall and leads into the enclosed interior space and a cutting edge that extends outward from the first exterior wall and is disposed at least partly above the aperture to contact against the first vertebral member when the implant is inserted into the patient;
   the enclosed interior space configured to capture and maintain portions of the first vertebral member that are removed by the plurality of features and enter through the apertures;
   a first set of plurality of features is oriented in a first direction on the first exterior wall and a second set of the plurality of features is oriented in an opposite second direction on the first exterior wall.

14. The implant of claim 13 further comprising a second plurality of features positioned about the second exterior wall with each of the second plurality of features including an aperture that extends through the second exterior wall and into the enclosed interior space and a cutting edge that extends outward from the second exterior wall to contact against the second vertebral member when the implant is inserted into the patient.

15. The implant of claim 13 wherein the plurality of features are spaced away from the sidewalls.

16. The implant of claim 13 wherein each of the cutting edges include a leading surface that is curved in a cutting direction and extends at least partially above the aperture.

* * * * *